US009018353B2

(12) United States Patent
Maini et al.

(10) Patent No.: US 9,018,353 B2
(45) Date of Patent: Apr. 28, 2015

(54) PROCESS FOR PRODUCING INSTANTANEOUS COLD SOLUBLE GELATIN AND PRODUCT THEREOF

(75) Inventors: Enrico Maini, Santa Maria della Versa (IT); Michele Maini, Santa Maria della Versa (IT)

(73) Assignee: Bioenol S.R.L., San Cipriano Po (PV) (IT)

( * ) Notice: Subject to any disclaimer, the term of this patent is extended or adjusted under 35 U.S.C. 154(b) by 370 days.

(21) Appl. No.: 13/390,274

(22) PCT Filed: Aug. 13, 2009

(86) PCT No.: PCT/IT2009/000384
§ 371 (c)(1),
(2), (4) Date: Mar. 22, 2012

(87) PCT Pub. No.: WO2011/018809
PCT Pub. Date: Feb. 17, 2011

(65) Prior Publication Data
US 2012/0178907 A1  Jul. 12, 2012

(51) Int. Cl.
C09H 3/00 (2006.01)
A23J 3/06 (2006.01)
A61K 9/20 (2006.01)
A61K 9/16 (2006.01)
C09H 9/00 (2006.01)
B01J 2/16 (2006.01)
C08H 1/06 (2006.01)
C08J 3/12 (2006.01)
C08L 89/06 (2006.01)
C09H 9/04 (2006.01)
A61K 38/00 (2006.01)

(52) U.S. Cl.
CPC ............... *A23J 3/06* (2013.01); *A61K 9/2063* (2013.01); *A61K 9/1658* (2013.01); *A61K 9/16* (2013.01); *C09H 3/00* (2013.01); *C09H 9/00* (2013.01); *B01J 2/16* (2013.01); *C08H 1/06* (2013.01); *C08J 3/12* (2013.01); *C08J 2389/06* (2013.01); *C08L 89/06* (2013.01); *C09H 9/04* (2013.01); *C08J 3/122* (2013.01)

(58) Field of Classification Search
CPC ............... C09H 7/00; C09H 5/00; C09H 3/00
See application file for complete search history.

(56) References Cited

U.S. PATENT DOCUMENTS

| 2,841,498 | A | * | 7/1958 | Cahn et al. | 426/576 |
| 3,341,334 | A | * | 9/1967 | Mitchell et al. | 426/576 |
| 3,892,876 | A | * | 7/1975 | Hobday et al. | 426/576 |
| 3,904,771 | A | * | 9/1975 | Donnelly et al. | 426/576 |
| 3,927,221 | A | * | 12/1975 | Kalafatas et al. | 426/576 |
| 3,930,052 | A | * | 12/1975 | De Brou et al. | 426/576 |
| 4,407,836 | A | * | 10/1983 | Bosco et al. | 426/576 |
| 4,409,255 | A | * | 10/1983 | Danielson et al. | 426/576 |
| 4,615,896 | A | * | 10/1986 | Brown et al. | 426/576 |
| 4,615,897 | A | * | 10/1986 | Brown et al. | 426/576 |
| 4,615,898 | A | * | 10/1986 | Brown et al. | 426/576 |
| 4,729,897 | A | * | 3/1988 | Poppe et al. | 426/96 |
| 4,732,758 | A | * | 3/1988 | Hurion et al. | 424/94.2 |
| 4,889,920 | A | * | 12/1989 | Muller | 530/355 |
| 5,384,129 | A | * | 1/1995 | Wunderlich et al. | 424/451 |
| 5,958,660 | A | * | 9/1999 | Taylor et al. | 430/537 |
| 6,066,352 | A | * | 5/2000 | Ogasawara et al. | 426/549 |
| 6,465,010 | B1 | * | 10/2002 | Lagoviyer et al. | 424/464 |
| 7,393,928 | B2 | * | 7/2008 | Chang et al. | 530/354 |
| 8,637,081 | B2 | * | 1/2014 | Gaissmaier et al. | 424/484 |
| 2004/0121949 | A1 | * | 6/2004 | Bonanomi et al. | 514/12 |
| 2005/0069514 | A1 | * | 3/2005 | Maleedy | 424/70.24 |
| 2005/0229264 | A1 | * | 10/2005 | Chang et al. | 800/8 |
| 2009/0062233 | A1 | * | 3/2009 | Ji et al. | 514/60 |
| 2009/0143568 | A1 | * | 6/2009 | Chang et al. | 530/354 |
| 2009/0285963 | A1 | * | 11/2009 | Dick et al. | 426/576 |

FOREIGN PATENT DOCUMENTS

| JP | 61-163963 | 7/1986 |
| JP | 2001-181580 | 7/2001 |
| WO | WO 2004/065507 A1 | 8/2004 |

OTHER PUBLICATIONS

International Search Report for PCT/IT2009/000384, mailed May 20, 2010.
Written Opinion of the International Searching Authority for PCT/IT2009/000384, mailed May 20, 2010.
Russian Office Action issued Jun. 14, 2013 and its English translation for Russian App 2012109419 corresponding to PCT/IT2009/000384 filed Aug. 13, 2009.

* cited by examiner

*Primary Examiner* — Maryam Monshipouri
*Assistant Examiner* — Samuel Liu
(74) *Attorney, Agent, or Firm* — Nixon & Vanderhye, PC

(57) ABSTRACT

Process for producing instantaneous cold soluble gelatin in form of agglomerates of gelatin granules carried out in a fluid bed under controlled temperature, which comprises soaking the gelatin granules through atomizing a granulating liquid in the fluid bed, where the granulating liquid is made up of water.

18 Claims, 5 Drawing Sheets

A

C

B

D

PROCESS FOR PRODUCING INSTANTANEOUS COLD SOLUBLE GELATIN AND PRODUCT THEREOF

This application is the U.S. national phase of International Application No. PCT/IT2009/000384, filed 13 Aug. 2009, which designated the U.S., the entire contents of which is hereby incorporated by reference.

FIELD OF THE INVENTION

The present invention concerns a process for producing pure instantaneous cold soluble gelatin and the respective pure instantaneous cold soluble gelatin thus obtained.

PRIOR ART

Gelatin is a natural polymer obtained through extraction of the collagen contained in the animal connective tissues—preferably bovines, pigs and fish—in hot water after a partial acid or alkaline hydrolysis.

Hydrolysis breaks down the bonds that bind the collagen chains to each other, making the protein soluble.

After being extracted, the gelatin solution, subjected to physical and chemical purification, is concentrated for evaporation under vacuum, sterilised, cold transformed into gel and lastly extruded in granules or thin layers and dried under currents of dry air.

This is the process for obtaining standard gelatin, which, being cold-dried, in solid state reproduces a triple-helix structure similar to that of the original gelatin.

The main characteristic of the gelatin is that of being transformed into reversible gel. By cooling a gelatin solution, the later acquires a consistency increasing depending on the concentration, purity and Bloom value of the product used.

Over the years, gelatin has been used in many applications both in the food sector as an ingredient in chewy sweets and in the food industry as a thickener, gelling agent, emulsifying agent and emulsion stabiliser. In the pharmaceutical industry it is used for manufacturing shells for both rigid and soft capsules. Over the last years, gelatin has also been used for "light" foods, especially due to the characteristic of dissolving in the mouth in a manner similar to fats.

However, use—especially at industrial level—of standard gelatin has a limiting factor: cold pre-dispersion—in water—of the gelatin in form granules or thin layers followed by the heating of the suspension to obtain a homogeneous solution is required.

The step of cold predispersion in water represents a problem, in that extremely difficult due to the formation of lumps. Furthermore, the subsequent heating represents a further industrial step, not always easy, inexpensive or technologically convenient.

Thus, over the years, men skilled in the art have tried to outline processes for producing instantaneous cold soluble gelatin, capable of being used avoiding carrying out operations of cold predispersion of gelatin and heating the obtained solution.

Such processes are concentrated in two main concepts: a) preparing instantaneous cold soluble gelatin by mixing gelatin with additional hydrophile ingredients and b) preparing instantaneous cold soluble gelatin through granulation of the gelatin to obtain granules having dimensions such to prevent formation of lumps.

Mixing gelatin with additional ingredients is, currently, the preferred practice. The main additional ingredients are selected from among i) sugars and/or maltodextrine, as observed for example from patent documents U.S. Pat. No. 4,615,897, U.S. Pat. No. 4,588,602, U.S. Pat. No. 4,615,896, U.S. Pat. No. 4,615,898, U.S. Pat. No. 4,571,346, U.S. Pat. No. 4,409,255, U.S. Pat. No. 4,407,836, U.S. Pat. No. 4,401,685, U.S. Pat. No. 3,927,221, U.S. Pat. No. 3,362,830, U.S. Pat. No. 2,948,622, U.S. Pat. No. 4,407,836, EP 0193378, EP 0087317, GB 1230531 and FR 2012559, and ii) food acids, sweeteners and/or various ingredients, as observed for example from U.S. Pat. No. 3,904,771, U.S. Pat. No. 3,868,465, U.S. Pat. No. 2,948,622, U.S. Pat. No. 3,607,306, U.S. Pat. No. 3,930,052.

These applications have the main drawback of bonding gelatin to other ingredients, a condition that limits their use in preparations that cannot contain such additional ingredients in their composition.

Regarding the granulation processes, these provide for hydrolysing and atomising gelatin before granulation as described in U.S. Pat. No. 4,889,920, or compulsorily using the hydrolysed gelatin as granulating liquid as described in the patent application WO 2004/065507.

Furthermore, application WO 2004/065507 states that a granulation process in a fluid bed granulator in which the gelatin particles are soaked only using water or water vapour does not allow obtaining instantaneous cold soluble gelatin, in that the gelatin powder particles in the step of soaking using water alone become sticky and form lumps in more or less consistent masses. In addition, deposits—which should be eliminated within a relatively short period of time so as not to jeopardise the operability of the granulator itself—form on the walls of the granulator. Furthermore, the product thus obtained does not dissolve instantaneously in cold aqueous liquids according to the traditional criteria and forms lumps under stirring.

The pre-hydrolysis process used in the process described in U.S. Pat. No. 4,889,920 and the use of granulating liquid based on hydrolysed gelatin as described in WO 2004/065507 however implies various disadvantages, among which the main one being the reduction of the mean molecular weight of the gelatin, thus its Bloom value with the ensuing reduction of the quality of the product and impossibility to obtain a cold soluble gelatin with high Bloom value. As a matter fact, should the granulation be carried out with a solution of hydrolysed gelatin as described in WO 2004/065507, a gelatin with lower gelling properties (Bloom value) than the initial gelatin is obtained due to the dilution of the initial gelatin with high molecular weight using the one hydrolysed at zero Bloom.

OBJECT AND SUMMARY OF THE INVENTION

An object of the present invention is providing a process for producing pure instantaneous cold soluble gelatin not having the disadvantages of the prior art.

According to the present invention, the abovementioned object is attained due to the solution specifically referred to in the claims that follow, which form an integral part of the present invention.

An embodiment of the invention concerns a process for producing instantaneous cold soluble gelatin in form of agglomerates of gelatin granules performed in a fluid bed granulator at controlled temperature, which comprises soaking gelatin granules through atomisation of a granulating liquid in the fluid bed, where the granulating fluid is represented by water.

Such process does not provide for a step of pre-hydrolysing and atomising gelatin before granulation or use of hydrolysed gelatin as granulating liquid avoiding the drawbacks linked to such technological solutions.

BRIEF DESCRIPTION OF THE DRAWINGS

Now, the invention shall be described, purely for exemplifying purposes, with reference to the figures of the attached drawings, wherein.

DETAILED DESCRIPTION OF EMBODIMENTS

Provided in the following description, are various specific details for complete understanding of the embodiments. The embodiments may be obtained without one or more of the specific details, or through other methods, components, materials, etc. In other cases, widely known structures, materials or operations are not shown or described in detail to avoid obscuring aspects of the embodiments.

During the entire description, reference to "an embodiment" is used to indicate that a particular aspect, structure, or characteristic described regarding the embodiment is included in at least one embodiment. Hence, the use of the expression "in an embodiment" in various points over this description does not necessarily refer to the same embodiment. Furthermore, the particular aspects, structures, or characteristics may be combined in any convenient manner into one or more embodiments.

References provided herein are solely for the sake of convenience and do not interpret the object or meaning of the embodiments.

Figure 1:
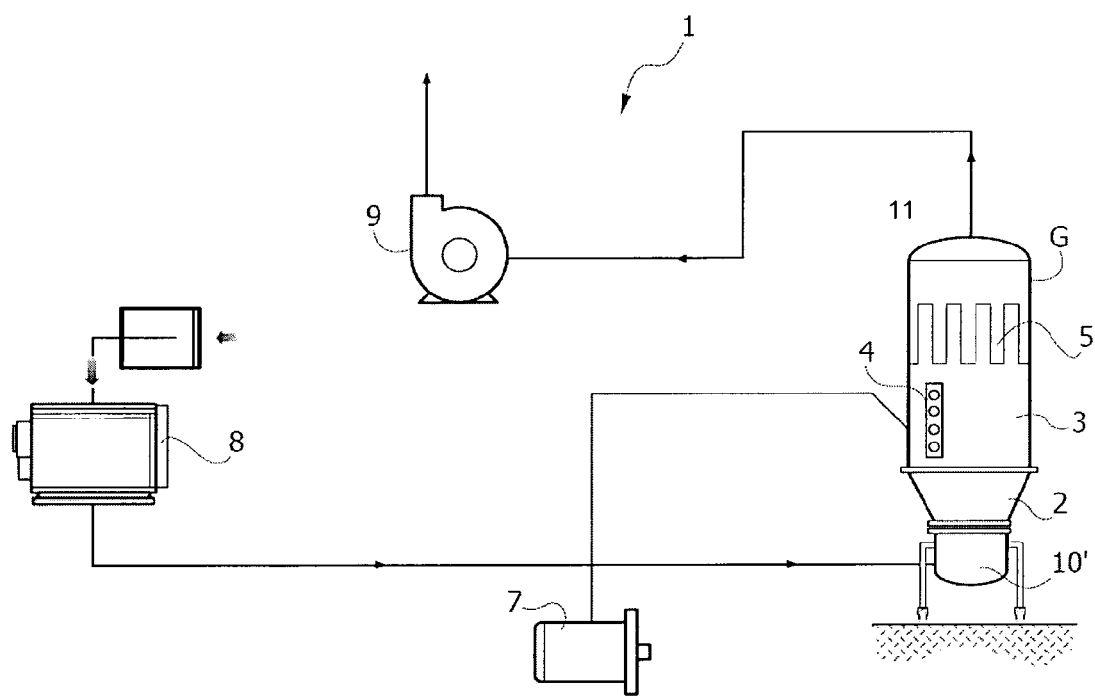
FIG. 1 shows a diagram of a fluid bed granulator device.

The process subject of the present description provides for the use of a fluid bed granulator schematically illustrated in FIG. 1.

A fluid bed granulator 1 useable to implement the process described herein consists of:
 a granulation chamber G;
 a system for introducing and alternatively heating an aeriform substance 8 into the granulation chamber G;
 a pump 7, preferably with adjustable flow rate, for introducing a granulating liquid into the granulation chamber G,
 hydro-pneumatic nozzles 4, preferably of the binary type, accommodated in the granulation chamber G, for atomising the granulating liquid, and,
 optionally, a fan 9 for extracting air from the granulation chamber G.

Operating from the bottom to the top, the granulation chamber G is divided into five sections in fluid communication with each other: a section for introducing the aeriform substance 10, a section 2 containing the product to be granulated, a turbulence section 3 for the growth of granules of the product to be granulated, a section 5 for filtering the aeriform substance and a section 11 for extracting the aeriform substance accommodated in such section being a fan (not illustrated) for suctioning air.

Generally, a fluid bed granulator operates as follows.

The powder to be granulated, gelatin in this case, is poured into the containment section 2 of the granulation chamber G.

Inside the turbulence section 3 the product is subjected to fluidisation (mixing) with an aeriform substance, preferably air. The aeriform substance is introduced into the granulation chamber G through the section 10 for introducing the aeriform substance and suctioned by the fan in the section for extracting the aeriform substance 11, in such a manner to create a fluid bed.

Granulation occurs in the turbulence section 3 by injecting a granulating liquid supplied by the pump 7 by means of nozzles 4. In this step, the particles agglomerate up to forming granule agglomerates having variable physical characteristics depending on the parameters and processing times.

Subsequently, injection of the granulating liquid is suspended and the granule agglomerates formed are subjected to drying through introduction—into the granulation chamber G—of a hot aeriform substance, heated by the system for introducing and heating the aeriform substance 8. The hot aeriform substance is introduced into the granulation chamber G through the section for introducing the aeriform substance 10.

Before being released into the atmosphere through the fan 9 the exhausted aeriform substance, is filtered in the filtration section 5.

The present inventors identified the operative conditions to be used in a fluid bed granulator capable of allowing producing an instantaneous cold soluble gelatin. In particular, the present inventors are capable of controlling the agglomeration of the gelatin particles so as to obtain gelatin in form of agglomerates of granules with high Bloom value capable of being cold-solubilised in an instantaneous manner without formation of lumps.

The present inventors observed that the final result is mainly influenced by: the composition of the granulating liquid and the quality and/or the flow rate of the spray of the granulating liquid sprayed/atomised on the initial gelatin.

Furthermore, the final result is influenced by the temperature maintained in the turbulence section 3 during the granules agglomeration step.

Further parameter influencing the result is given by the temperature maintained in the turbulence section 3 during the drying step and by the duration of such step.

In particular, it is important to check whether both during the granules agglomeration step and during the drying step the temperature difference between the in-flowing and out-flowing air, i.e. between the air introduced into the granulation chamber before coming into contact with the gelatin granules/agglomerates and the air released from the granulation chamber after coming into contact with the gelatin granules/agglomerates, is constant and/or whether the temperature of the product during the granules agglomeration and drying step remains constant.

Described hereinafter is a preferred embodiment of the process subject of the present invention.

The solid mass to be treated is made up of a gelatin powder obtained through grinding particles with maximum size amounting to about 300 μm, with moisture in the range between 4-10% w/w, preferably 5-8% w/w, even more preferably 6-6.5% w/w.

The granulating liquid is made up of water at ambient temperature, the water is finely sprayed/atomised onto the gelatin powder through the peristaltic pump 7 and nozzles 4, using, preferably, filtered compressed, deoiled and dry air as the atomising agent.

As soon as it is introduced into the granulation chamber, the gelatin powder is subjected to a pre-heating step by introducing a hot aeriform substance until a temperature of about 40° C. is reached, then the atomisation of the granulating liquid begins at a flow rate such to maintain the temperature of the gelatin powder in the range between 35-45° C., which in the operating conditions used is comprised between 200 and 300 cc/min.

The amount of granulating liquid used in the atomising step is comprised between 150 and 350 cc/50 kg, preferably between 225 and 275 cc/50 kg, even more preferably equivalent to 250 cc/50 kg.

The temperature of the aeriform substance entering into the granulation chamber and, in particular, in the turbulence section is maintained in the range between 50-75° C.

At the end of the granules agglomeration step, the agglomerated gelatin is maintained in fluid phase by the airflow in the turbulence section for a period of time such to attain a final moisture of the agglomerated gelatin in the range between 4.0-4.5% w/w.

At this point the agglomerated gelatin may be released and left to cool at ambient temperature before repartitioning.

The instantaneous cold soluble gelatin produced through the process described above is cold soluble without requiring dilution with any hydrophilic dispersing agent.

The agglomerated gelatin is as illustrated in FIGS. 5A-5D. Such gelatin is made up of a sponge-like agglomerate of gelatin granules, where such structure facilitates diffusion of water in the mass and allows cold dissolution of the product.

An instantaneous cold soluble gelatin with moisture content at around 4-5% and an increase of the Bloom value due to the increase of the protein value are obtained through the process described above using a standard gelatin with moisture value at around 10% as the initial gelatin. Table 1 shows the increase of Bloom value when the gelatin is produced through the process described herein.

TABLE 1

| Sample | Initial gelatin Bloom value | instantaneous cold soluble gelatin Bloom value |
|---|---|---|
| C081013/A | 200 | 212 |
| C081013/B | 200 | 212 |
| C090122/A | 200 | 212 |
| 90529/A | 200 | 216 |
| 90530/A | 220 | 229 |

Solubility Test

The gelatin produced using the process described herein has an improved solubility with respect to gelatins produced according to processes of the prior art.

The solubility test was performed taking into account the following types of gelatin:

i) a standard gelatin obtained through drying from the gel state, extracted from pigs, with 220 Bloom value and 70 mesh particle size distribution, ii) an instantaneous cold soluble gelatin dried on a heated drum and ground, extracted from pigs, with 220 Bloom value and 140 mesh particle size distribution, and iii) an instantaneous cold soluble gelatin produced through the process described herein, extracted from pigs, with 220 Bloom value and 40/50 mesh particle size distribution.

The solubility test was performed by adding 2.5 g of gelatin in 100 mL of distilled water at a temperature of 25° C. without stirring.

The results of the observation are indicated in table 2.

TABLE 2

| Type of gelatin | Solubility |
|---|---|
| *After 1 hour* | |
| i) standard gelatin | Undissolved granules present, solution considerably heterogeneous |
| ii) instantaneous cold soluble gelatin produced according to the prior art | Gelatinous lumps start forming, non-homogeneous solution |
| iii) instantaneous cold soluble gelatin produced according to the process described herein | Almost uniform solution, very few and extremely small lumps |
| *After 2.5 hours* | |
| i) standard gelatin | Some undissolved granules still present, solution considerably heterogeneous |
| ii) instantaneous cold soluble gelatin produced according to the prior art | The solution has large gelatinous lumps, non-homogeneous solution |
| iii) instantaneous cold soluble gelatin produced according to the process described herein | Uniform solution, almost homogenous, very few lumps |
| *After 5 hours* | |
| i) standard gelatin | Few undissolved granules, heterogeneous solution |
| ii) instantaneous cold soluble gelatin produced according to the prior art | Large gelatinous lumps still present, non-homogeneous solution |
| iii) instantaneous cold soluble gelatin produced according to the process described herein | Uniform solution |

Table 2 shows that the instantaneous cold soluble gelatin iii) produced through the process described herein has a better solubility not only with respect to the standard gelatin i), but also with respect to an instantaneous cold soluble gelatin ii) produced according to the known art. In particular, an instantaneous cold soluble gelatin produced through the process described herein leads to obtaining a uniform homogeneous solution just after 2.5 hours, while an instantaneous cold soluble gelatin ii) produced according to the prior art still has large gelatinous lumps and hence a non-homogeneous solution, such gelatinous lumps remain even after 5 hours in water.

Differential Scanning Calorimetry Measurements

All differential scanning calorimetry measurements DSC represented by the charts of FIGS. 6-9 were carried out using a Perkin Elmer Pyris Diamond DSC, provided with an intracooler model ULSP 90. The instrument was calibrated through high purity standards (n-decane and indium).

The analysis were carried out in the temperature range between 45°-180° C. with a scanning speed of 5° C./min using a hermetically sealed pan and under nitrogen flow. The analysed samples have a weight comprised in the range between 3-6 mg.

Figure 2:
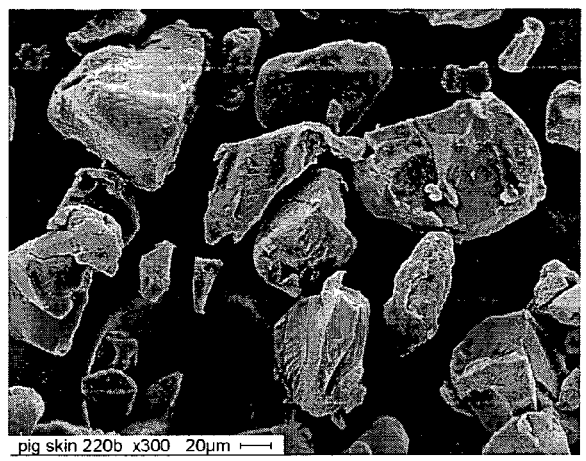
FIG. 2 shows a scanning electron microscope photograph of a standard gelatin.
Figure 3:
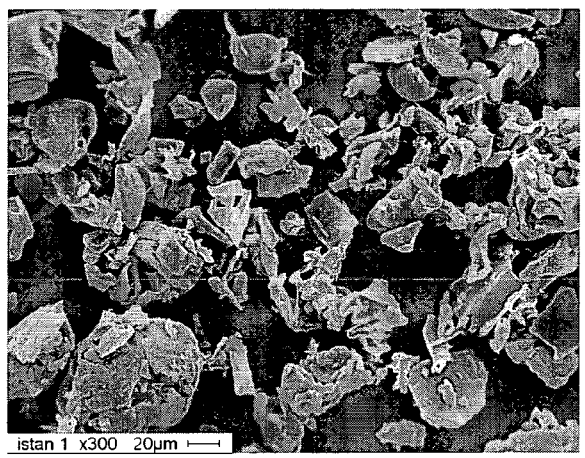
FIGS. 3 and 4 show two scanning electron microscope photographs of two instantaneous gelatins dried on a heated drum with particle size distribution equivalent to about 140 mesh.
Figure 4:
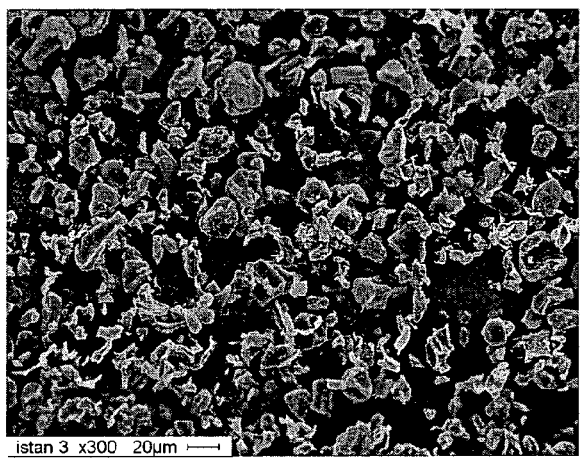
Figure 5:
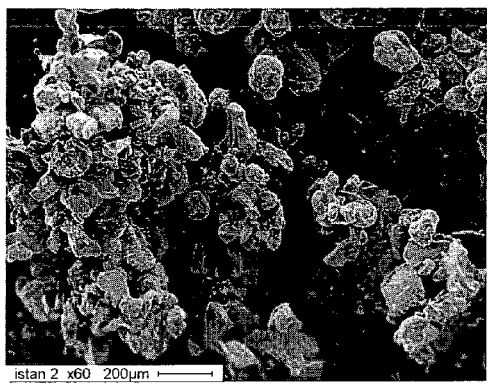
FIGS. 5A-5D show four scanning electron microscope photographs of cold soluble instantaneous gelatins produced according to the process described herein with particle size distribution equivalent to about 40/50 mesh.
Figure 5:
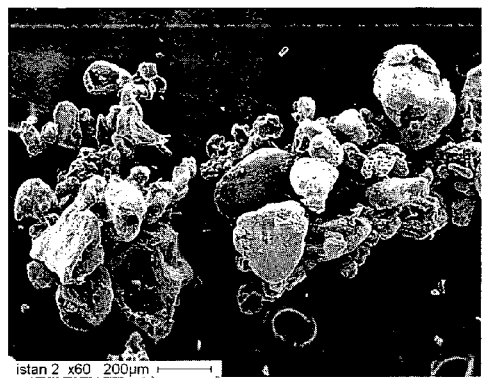
Figure 5:
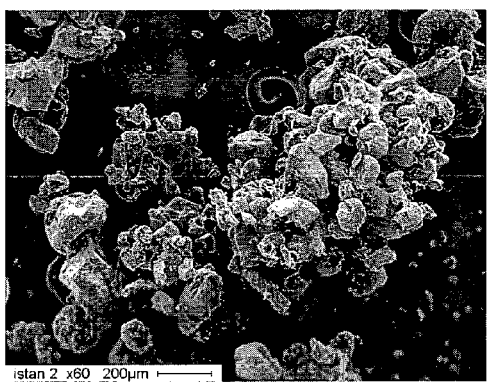
Figure 5:
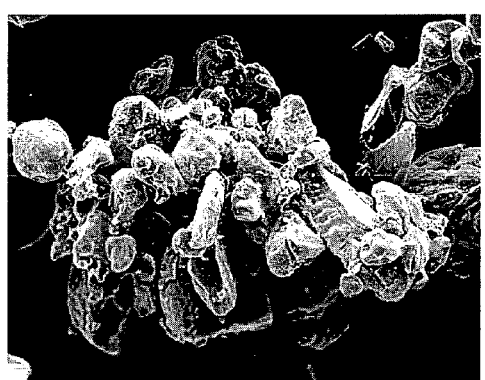

The analysed gelatins were:

i) a standard gelatin produced through drying from the gel state, which—regardless of the degree of fragmentation—appears under the electronic microscope in form of pebbles as shown in FIG. 2;

ii) an instantaneous gelatin obtained directly from drying a solution through evaporating water on a vapour heated drum without passing through the gel phase, which appears under the electronic microscope in form of scales as shown in FIGS. 3 and 4;

iii) an instantaneous cold soluble gelatin produced according to the process subject of the present application, which appears in agglomerated form as illustrated in FIGS. 5A-5D.

Figure 6:
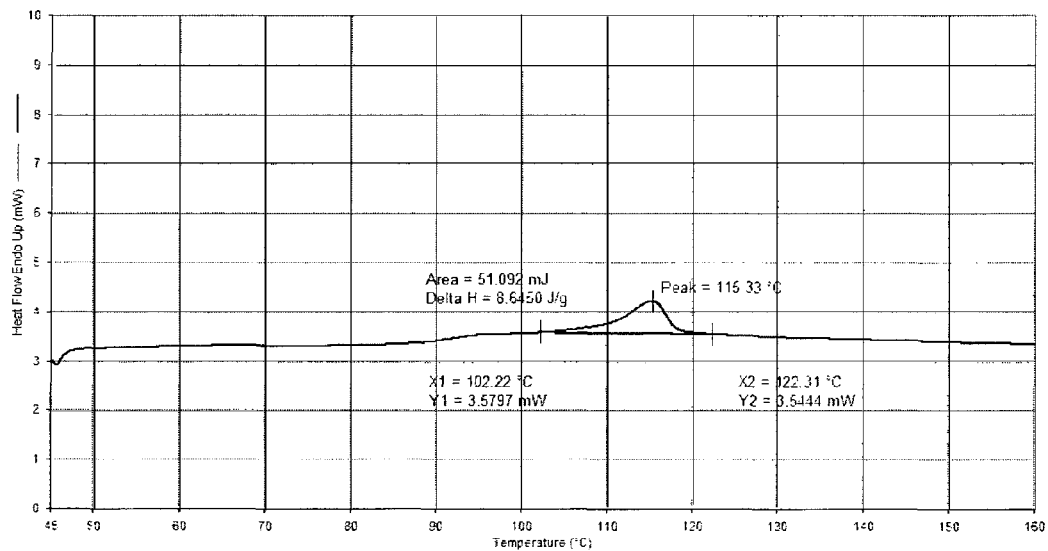
FIG. 6 represents a chart for differential scanning calorimetry measurement of a standard gelatin.

The standard gelatin i) has bonds similar to those of the initial collagen and shows an energy absorption due to the denaturing of such bonds at 115° C. as shown in FIG. 6.

Figure 7:
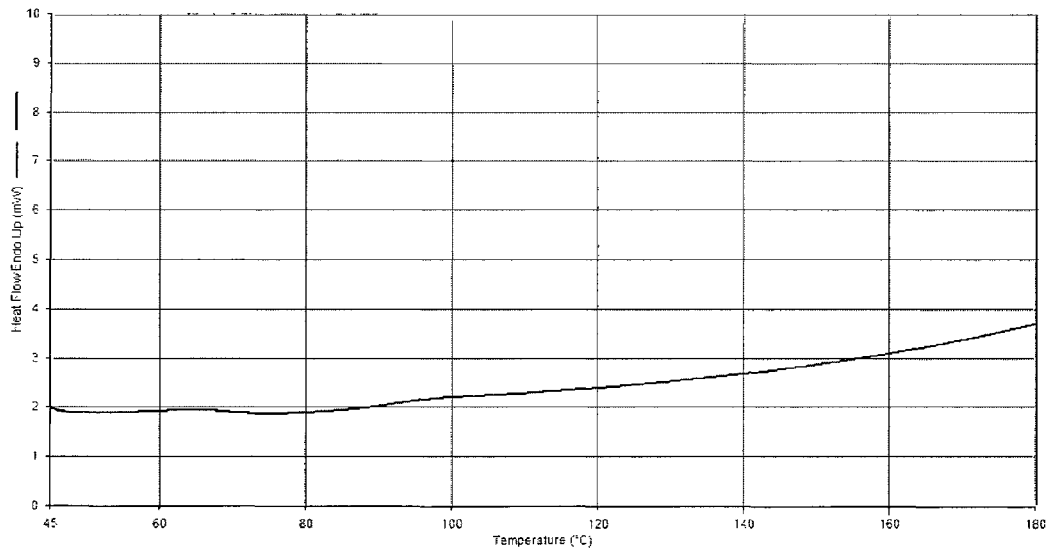
FIGS. 7 and 8 represent charts for differential scanning calorimetry measurements of a gelatin produced by drying a gelatin solution through evaporation on a heated drum.

The instantaneous gelatin ii) has no triple-helix bonds typical of the standard gelatin i), as shown by the absence of peaks of FIG. 7. Such gelatin is soluble in cold water only if well dispersed together with other ingredients having hydrophilic characteristics, which are necessary to allow the diffusion of water in the mass of the gelatin itself.

Figure 8:
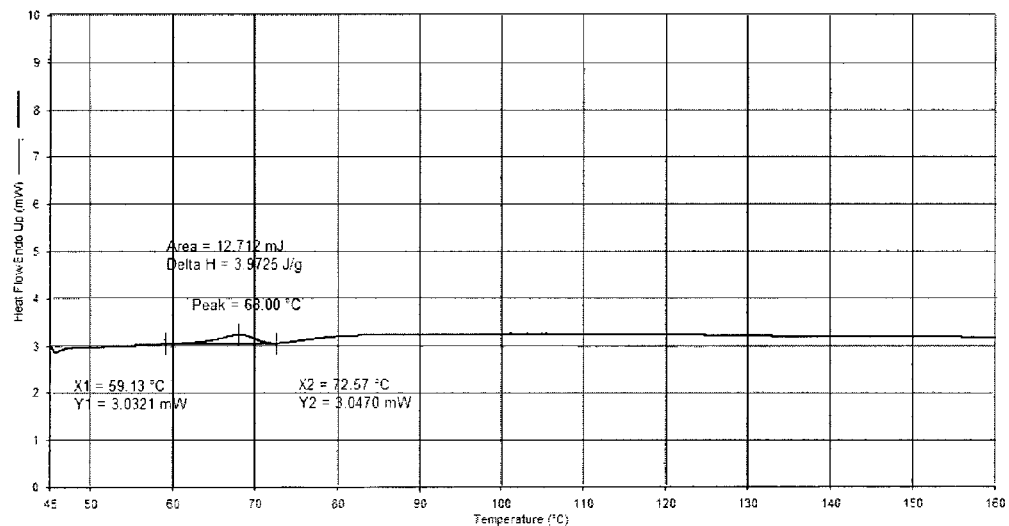

Examining a second instantaneous gelatin ii), such gelatin has characteristics similar to those of the gelatin of FIG. 7 as shown in FIG. 8.

Figure 9:
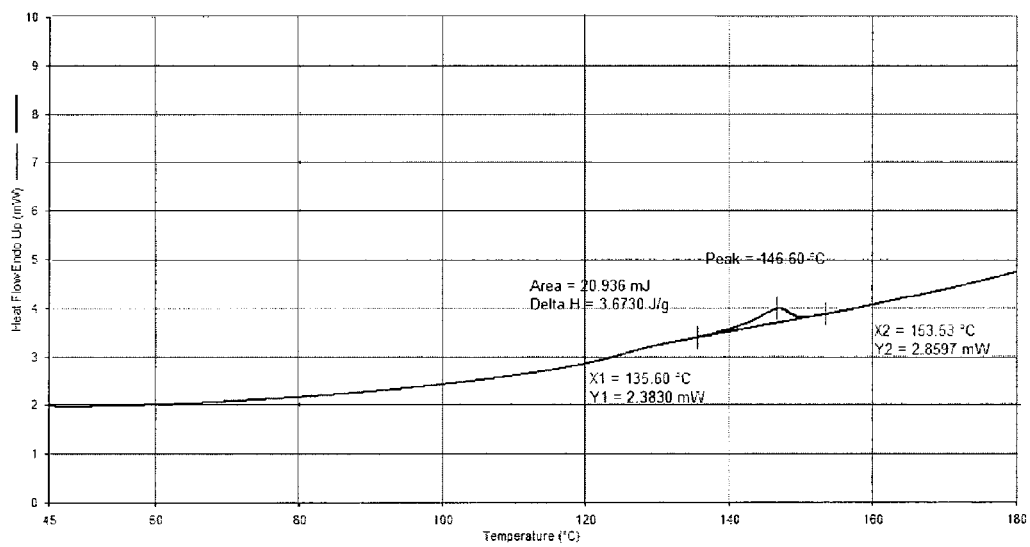
FIG. 9 represents a chart for differential scanning calorimetry measurement of an instantaneous cold soluble gelatin produced according to the process described herein.

The instantaneous gelatin iii) is subjected to thermal analysis to check the presence of stable bonds similar to those of collagen. FIG. 9 shows an energy absorption of the gelatin iii) due to the denaturing of triple-helix bonds at a temperature equivalent to 146° C. with an enthalpy variation of 3.67 J/g. The denaturing temperature is higher with respect to the denaturing temperature of standard gelatin i) (146° C. vs 115° C.) and this indicates greater stability of the gelatin iii) produced according to the process described herein.

Furthermore, the instantaneous cold soluble gelatin iii) has lower enthalpy variation with respect to that of standard gelatin i) (3.67 J/g vs 8.64 J/g, see FIGS. 6 and 9), thus indicating fewer triple-helix bonds, i.e. a substantial and measurable difference between the products.

The graphic trend in FIG. 9 shows substantial differences with respect the charts of FIGS. 6-8, both in terms of the peak height and the respective denaturing temperature. In particular, an instantaneous cold soluble gelatin not requiring pre-dispersion before use, the structure of the collagen already being open, is obtained by implementing the process described herein. The gelatin produced according to the process described herein does not have a substantial number of triple-helical bonds, which were almost entirely denatured during the production process.

The invention claimed is:

1. A process for producing a dry instantaneous cold water soluble gelatin in the form of agglomerates of gelatin granules, said process being carried out in a fluid bed comprising an aeriform substance under a controlled temperature, said process comprising soaking said gelatin granules through atomizing a granulating liquid in said fluid bed, wherein said granulating liquid consists of water and wherein soaking of said gelatin granules with said granulating liquid allows for the formation of said agglomerates at a first temperature and drying said gelatin agglomerates moving in said fluid bed at a second temperature.

2. The process according to claim 1, comprising maintaining the difference between the temperature of the aeriform substance of said fluid bed flowing into said fluid bed and the temperature of the aeriform substance in said fluid bed flowing out from said fluid bed constant.

3. The process according to claim 1, wherein said first temperature is between 50 and 75° C.

4. The process according to claim 1, wherein said second temperature is between 50 and 75° C.

5. The process according to claim 1, wherein said formation of said agglomerates and said drying of said agglomerates are carried out in conditions to maintain said first and said second temperature of the aeriform substance constant.

6. The process according to claim 1, further comprising an initial preheating of said gelatin granules introduced into said fluid bed at a third temperature, before soaking said gelatin granules.

7. The process according to claim 6, wherein said third temperature is comprised between 35 and 45° C.

8. The process according to claim 7, wherein said third temperature is 40° C.

9. The process according to claim 1, wherein said gelatin granules have a particle size not exceeding 450 microns.

10. The process according to claim 9, wherein said gelatin granules have a particle size not exceeding 400 microns.

11. The process according to claim 9, wherein said gelatin granules have a particle size not exceeding 300 microns.

12. The process according to claim 1, wherein said gelatin granules have an initial humidity between 4 and 10% w/w.

13. The process according to claim 12, wherein said gelatin granules have an initial humidity between 5 and 8% w/w.

14. The process according to claim 12, wherein said gelatin granules have an initial humidity between 6 and 6.5% w/w.

15. The process according to claim 1, wherein said atomisation of said granulating liquid is carried out at a granulating liquid flow rate comprised between 200 and 300 cc/min.

16. The process according to claim 1, wherein said atomisation of said granulating liquid is carried out using an amount of granulating liquid between 150 and 350 cc/50 kg.

17. The process according to claim 16, wherein said atomisation of said granulating liquid is carried out using an amount of granulating liquid between 225 and 275 cc/50 kg.

18. The process according to claim 16, wherein said atomisation of said granulating liquid is carried out using an amount of granulating liquid of 250 cc/50 kg.

* * * * *